United States Patent
Berry et al.

(10) Patent No.: US 9,605,325 B2
(45) Date of Patent: *Mar. 28, 2017

(54) MIXED SUPER CRITICAL FLUID HYDROLYSIS AND ALCOHOLYSIS OF CELLULOSE TO FORM GLUCOSE AND GLUCOSE DERIVATIVES

(71) Applicant: INVENTURE RENEWABLES, INC., Tuscaloosa, AL (US)

(72) Inventors: William W. Berry, Tuscaloosa, AL (US); William Rusty Sutterlin, Tuscaloosa, AL (US); Mark G. Tegen, Tuscaloosa, AL (US)

(73) Assignee: Inventure Renewables, Inc., Tuscaloosa, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/163,160

(22) Filed: May 24, 2016

(65) Prior Publication Data
US 2016/0281183 A1 Sep. 29, 2016

Related U.S. Application Data

(63) Continuation of application No. 13/882,986, filed as application No. PCT/US2011/058835 on Nov. 1, 2011, now Pat. No. 9,346,843.

(60) Provisional application No. 61/409,395, filed on Nov. 2, 2010.

(51) Int. Cl.
| | | |
|---|---|---|
| *C13K 1/02* | (2006.01) | |
| *C07H 1/00* | (2006.01) | |
| *C08H 8/00* | (2010.01) | |
| *C12P 7/06* | (2006.01) | |

(52) U.S. Cl.
CPC ............ *C13K 1/02* (2013.01); *C07H 1/00* (2013.01); *C08H 8/00* (2013.01); *C12P 7/06* (2013.01); *A23V 2002/00* (2013.01); *C12P 2203/00* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 3,375,243 | A * | 3/1968 | Nevin | C07H 15/04 536/18.6 |
| 4,223,129 | A * | 9/1980 | Roth | B01J 19/243 536/120 |
| 2009/0176286 | A1* | 7/2009 | O'Connor | C08B 37/0003 435/139 |
| 2009/0198077 | A1 | 8/2009 | Berry et al. | |
| 2009/0217922 | A1 | 9/2009 | Fukuoka et al. | |
| 2010/0069626 | A1* | 3/2010 | Kilambi | C08H 8/00 536/56 |
| 2010/0175690 | A1 | 7/2010 | Nagahama et al. | |
| 2011/0245444 | A1* | 10/2011 | Miller | C07C 9/00 526/346 |

FOREIGN PATENT DOCUMENTS

| | | | |
|---|---|---|---|
| EP | 2226335 A1 | 9/2010 | |
| JP | 2001170601 A | 6/2001 | |
| NZ | WO 2010030196 A1 * | 3/2010 | .............. C07C 9/00 |
| WO | 2010009343 A2 | 1/2010 | |
| WO | 2010030196 A1 | 3/2010 | |

OTHER PUBLICATIONS

Huber et al, synthesis of transportation fuels from biomass: chemistry, catalysts and engineering, 2006, 106, pp. 4044=4098.*
SGINC1-07, composition of herbaceous biomass feedstock, 2007.*
Huber et al, "Synthesis of transportation fuels from biomass: chemistry, catalysts, and engineering" Chemical Reviews, 2006, v 106, n 9, p. 4044-4098.
Lee et al, "Composition of herbaceous biomass feedstocks" South Dakota State University, 2007.
Latrigue, Supplementary European Search Report for EP 11838699, dated May 27, 2014.

* cited by examiner

*Primary Examiner* — Melvin C Mayes
*Assistant Examiner* — Stefanie Cohen
(74) *Attorney, Agent, or Firm* — Greer, Burns & Crain, Ltd.; Gregory P. Einhorn

(57) ABSTRACT

The present invention relates to a process for generating glucose and glucose derivatives from the direct contacting of cellulose, hemicelluloses and/or polysaccharides with a mixed super critical fluid system of alcohol and water whereby the partial pressure of the system provides for both alcoholysis and hydrolysis of the material to generate primarily glucose, and glucose derivatives.

27 Claims, No Drawings

MIXED SUPER CRITICAL FLUID HYDROLYSIS AND ALCOHOLYSIS OF CELLULOSE TO FORM GLUCOSE AND GLUCOSE DERIVATIVES

CROSS-REFERENCE TO RELATED APPLICATIONS

This application is a continuation of and claims benefit of priority under 35 U.S.C. §120, to pending U.S. application Ser. No. 13/882,986, filed on Jul. 31, 2013, now U.S. Pat. No. 9,346,843, issued May 24, 2016, which is a national phase application claiming benefit of priority under 35 U.S.C. §371 to Patent Convention Treaty (PCT) International Application serial no. PCT/US2014/053594, filed Aug. 29, 2014, which claims the benefit of priority under 35 U.S.C. §119(e) of U.S. Provisional Application Ser. No. (U.S. Ser. No.) 61/990,052, filed May 7, 2014; and U.S. Ser. No. 61/872,354, filed Aug. 30, 2013. The aforementioned applications are expressly incorporated herein by reference in their entirety and for all purposes.

FIELD OF THE INVENTION

The present invention relates to a process for generating glucose and glucose derivatives from the direct contacting of cellulose, hemicellulose, and/or polysaccharides with a mixed super critical fluid system of alcohol and water whereby the partial pressure of the system provides for both alcoholysis and hydrolysis of the material at reduced temperature and pressure.

BACKGROUND OF THE INVENTION

Due to the limited reserves of fossil fuels and worries about emission of greenhouse gases there is an increasing focus on using renewable energy sources.

Production of fermentation products from cellulose, hemicelluloses, lignocelluloses and polysaccharide containing residue materials is known in the art and includes pre-treating followed by, enzymatic hydrolysis, weak acid hydrolysis, strong acid hydrolysis, and supercritical water hydrolysis to generate fermentable residue materials. Acid hydrolysis has the potential to generate toxic compounds that can reduce or inhibit fermentation in addition to the consumption of substantial amounts of acid at a significant cost. Enzymatic hydrolysis reaction rates can be long as well as sensitive to foreign materials in the target residue, and the cost of enzymes can be expensive. Supercritical water hydrolysis requires capital cost intensive very high temperatures and pressures (>374 C and 22.1 Mpa) to achieve usable break down products. Acid hydrolysis, enzymatic hydrolysis and high pressure supercritical water hydrolysis are challenging methodologies for generating valuable fuels and chemicals from residue biomass. Consequently, there is a need for providing further methods and processes for producing fermentable glucose and glucose derivative products from residue materials using a time reduced system free of acid pretreatment, enzyme technology or very high pressure and temperatures to break down the cellulose linkage.

BRIEF SUMMARY OF THE INVENTION

Glucose and glucose derivates are produced from cellulose, hemicellulose, lignocellusoses and polysaccharide containing residue materials as follows: (a) combining size reduced cellulose, hemicelluloses, lignocelluloses and polysaccharide containing residue materials with alcohol from 0.1:1 to 100:1 by weight and water from 0.1:1 to 100:1 by weight to form a slurry (b) at a temperature in a range of 140° C. to 350° C., and at a pressure in a range of 500 psig to 3500 psig. (c) multiple reaction zones are established by permeable membrane or membranes which are used to trap the reaction mixture in the reaction zone. Once the reaction mixture of polysaccharide material is sufficiently cleaved to shorter chain materials they will become soluble and small enough to pass through the reaction zone membrane thereby minimizing reaction zone contact time (d) the reaction mixture can include hydrogen, (e) the reaction mixture can include a catalyst. The resulting reaction mixture is quenched and the un-reacted solids and non fermentable materials are separated from the glucose and glucose derivatives by activated carbon contacting.

DETAILED DESCRIPTION OF THE INVENTION

The present invention relates to a method for producing glucose and glucose derivatives by performing simultaneous hydrolysis and alcoholysis on a material containing polysaccharides, cellulose, hemicellulose, lignocellulose, or combination thereof with an alcohol, water, optionally a catalyst, an optionally hydrogen.

Prior to the present invention, the conversion of biomass into fermentable sugars was a time-consuming and multi-step procedure that was both economically inefficient and wasteful. Additionally, conventional methods are inhibited by the presence of water, require weak or strong acids, or the addition of expensive enzymes. In contrast a fast, single-step, and efficient method for the conversion of biomass into sugars or sugar derivatives to produce ethanol or industrial chemicals can be performed under a mixed supercritical fluid system whereby the presence of both water and alcohol work in combination to achieve the alcoholysis and hydrolysis at reduced temperature and pressure.

The feedstock for this process can be for example, palm fiber, palm fruit bunches, rice husk, rice straw, corn stover, corn cobs, sugar cane bagasse, switch grass, dried distillers grains (DDG) from, e.g., corn or sorghum, rice bran, eukaryota, protozoa, phytoplankton, cyanobacteria, bacteria, corn ethanol fermentation residuals, or other polysaccharide or cellulose-containing material (e.g., polysaccharides, cellulose, hemicellulose, and lignocellulose) or both.

The feedstock can contain from about 0 wt % to about 100 wt % cellulosic material (preferable less than about 70 wt %, but at least about 1, 5, 10, 15, 30 wt %). Each of the amounts for the feedstock components listed above is based on the dry weight of the feedstock.

The feedstock can be un-extracted meaning that it has not been purified to remove certain components (e.g., water, salt, foreign matter, or mixtures thereof). For example, the feedstock can contain at least about 5 wt % sails and up to 50 wt % salts. The feedstock can also be purified (e.g., a purified cellulose or paper pulp material). The feedstock can contain husks, shells, or other materials that are grown by the feedstock source other than the feedstock. The feedstock, prior to reaction, can be dried but the feedstock is preferred wet. The feedstock can be ground to reduce its particle size prior to reaction.

For purposes of this description, rice husk, rice straw, corn stover, wheat straw, corn cobs, sugar cane bagasse, switch grass, and woody biomass are used as the feedstock, however those skilled in the art would understand that other feedstock can be used. Also, the overall process, is as indicated, applicable to the other feedstocks with adjustments to the process configuration.

In addition, with other feedstocks, there may be some variations in the super critical alcoholysis and hydrolysis chemistry such that alternate co-products are formed in the reaction. For example, with a high cellulose feed (e.g., at least about 1, 5, 10, or 15 wt % but less than about 50, 60, 80 or 100 wt % based on the dry weight of the feedstock) there may be further conversion of that component to derivatized sugar compounds such as alkyl glucosides and 5-hydroxymethylfurfural. For example, when a solution of glucose in methyl alcohol is saturated with hydrochloric acid a crystallizable compound having the formula $C_6H_{11}O_6CH_3$, is formed.

A similar reaction takes place with all of the alcohols which are capable of dissolving glucose, such as methane, ethanol, propanol, butanol and their isomers, and the compounds formed correspond to natural glucosides. The sugar entering into the reaction need not necessarily be glucose, so that a number of such artificial alcohol-derivatized sugars can be prepared. The hydrochloric acid of the reaction to produce derivatized sugars can also be replaced by another acid such as $H_sSO_4$. These derivatized sugars, when boiled with dilute acid, react with water and are decomposed into the sugar and alcohol. In addition, further derivatization, in the presence or absence of acid or a catalyst, at the higher ranges of temperatures and pressures can lead to valuable products from the sugars such as methyl glucosides, ethyl glucosides, 5-hydroxymethylfurfural, levulinic acid, formic acid, and esters thereof. The categorization of each feedstock may be necessary to determine the best process splits and optimal end-products.

The alcohol for the invention can be, for example, methanol, ethanol, propanol butanol, isopropyl alcohol, sec-butanol, t-butanol, benzyl alcohol or combination thereof. From a practical standpoint, and for general fuel and potential downstream chemical considerations, alcohols containing from 1 to 5 carbons would be preferred, however, there may be specific situations and conditions wherein higher alcohols could be used. Testing with a specific alcohol would readily determine the amenability of a particular alcohol. Again, for purposes of this discussion, methanol is used us the alcohol, however those skilled in the art would understand that other alcohols can be used.

The feedstock can be ground to reduce its particle size and is then transferred to the Direct Mixed Supercritical Fluid Reactor system wherein the feedstock is mixed with the selected alcohol (e.g., methanol) and water. The amount of alcohol and water can vary, but would typically be sufficient to allow for a slurry mixture using equal pans of alcohol and water. This typically provides sufficient excess alcohol and water for the reaction noting that typically 30% by weight alcohol of the liquid mixture to 70% by weight water are required to achieve super critical partial pressure, under super critical conditions alcohols, e.g. methanol. Preferably, the alcohol should be in an amount from about 10% by mol to about 1000% by mol of the water, preferably from about 20% by mol to about 500% by mol of the water and most preferably from about 50% by mol to about 300% by mol of the water. Higher alcohols would require a higher weight percentage of alcohol. For practical operation, the amount of alcohol would normally be in the range of about 25 wt % to 300 wt % of the dry feedstock and preferably in the range of about 50 wt % to about 200 wt % of the dry feedstock.

The temperature of the reaction is in a range of about 240° C. to about 320° C., about 240° C. to about 270° C., or about 250° C. to about 280° C. The pressure of the reaction is a range of about 500-3200 psig, from about 1000-2000 psig, or from about 1500 to 2000 psig.

The reaction mixture before reaction can also contain water in an amount, of at least about 5 wt % of the dry weight of the feedstock, at least about 10 wt % of the dry weight of the feedstock, at least about 40 wt % of the dry weight of the feedstock, at least about 70 wt % of the dry weight of the feedstock, or at least about 100 wt % of the dry weight of the feedstock or at least about 200 wt % of the dry weight of the feedstock.

The reactor system can be batch or continuous. There are several conventional pressure vessel systems available that will operate in batch and continuous modes and the process lends itself to the "conventional" methods for this stage. In the continuous plug flow or continuous stir tank configuration a permeable membrane is used to trap the reaction mixture in the reaction zone to minimize resonance time in the zone.

In addition, a continuous pipe-type reactor can be used to carry out the reaction. The reactor is a pipe with sufficient residence time to allow for the reaction to complete and is operated under the target pressure and temperature range. The pipe allows for reasonable reaction to occur with minimized vessel complexity. In addition the pipe can contain zones separated by membranes whereby the reaction mixture will flow to the next contact zone after size reduction via hydrolysis occurs. This minimizes residence time in the reaction zone and reduces by-product formation.

The reaction can be carried out for a period of about 0.25 minutes to 240 minutes and the reaction time can depend on the selected reaction system and operating temperature. In a conventional stirred tank reactor, the reaction time can be in the range of 60 to 90 minutes for a batch reactor. At higher temperatures, and corresponding pressures, the reaction time can be reduced.

The reaction mixture can include hydrogen and can include a catalyst. The hydrogen can range from 1:1 mole wt of the glucose in the feedstock to 1000:1 mole wt of the contained glucose in the feedstock. The presence of hydrogen and/or a hydrogenation catalyst in the reaction mixture improves stability of the glucose by forming sorbitol or other polyhydric alcohols and sugar derivatives. Catalysts can be heterogeneous or homogenous. Catalysts metals can include platinum, palladium, rhodium, ruthenium, rainey nickel, and copper chromite.

The reaction product slurry typically consists of any unreacted feedstock, glucose, alkyl glucosides, sorbitol, excess alcohol, water, lignin, organic salts, inorganic salts, etc. The resulting glucose and alkyl glucosides will be in the range of 10-70 wt % of the product slurry. The reaction slurry is transferred to a Liquid/Solid Separation system. In this step, the liquid fraction is separated from the insoluble solids portion, including any lignin if continued in the feed. Separation can be carried out using any number of standard separation techniques, such as filtration, carbon treatment, centrifugation, combinations of each approach, and the like. Slight washing of the solids, in the separation device, can be carried out with a small amount of the alcohol, water, or hydrophobic solvent. The target glucose and alkyl glucoside materials remain with the liquid water phase.

The washed solids are then sent to storage for re-processing or discharge.

The alcohol and water is removed from the soluble fraction containing the glucose and alkyl glucoside by evaporation, centrifuge separation, crystallization or other method obvious to someone skilled in the art. The alcohol water mixture is then recycled back to the reaction mixture vessel where make up alcohol and water is added and new target feedstock is added.

The resulting glucose and methyl glucoside fraction is transferred to storage.

The alkyl glucoside can be optionally hydrolyzed using weak acid and additional water. The resulting mixture would be glucose and alcohol. The alcohol would be removed by evaporation, centrifuge separation, crystallization or other method obvious to someone skilled in the art.

The resulting glucose fraction is transferred to storage.

The glucose and/or glucose and alkyl glucoside then enters a Fermantation System wherein it is mixed with conventional fermentation reagents, e.g. yeasts, etc., then allowed to react in a conventional fashion. Information, relative to the conventional processing approaches are available on numerous web-sites, and a significant resource is the Renewable Fuels Association (available on the WorldWideWeb at rfa.org), which is the key industry trade association. The main advantage is that a potentially lower cost feedstock has now beat made available that does not involve a current agricultural food source commodity but rather second generation non food materials such as cellulose or agricultural by-products.

The fermentation slurry is then sent to a Solid/Liquid Separation system, and the non-fermented solids removed from the liquid (beer) phase. Again, conventional separation methods may be utilized, such as filters, centrifuges, and the like. The solids fraction can then be used elsewhere e.g. return to the algae farms as a supplemental food source.

The fermented liquid is transferred to an Evaporation System wherein the alcohol phase is evaporated from the liquid, along with some water.

The alcohol fraction is next treated in a Distillation/Molecular Sieve system. In this process step, the aqueous alcohol is first distilled, to produce a nominal 95% ethanol material, then processed in a molecular sieve unit to remove the remaining water and produce a 99.5%+ ethanol product (31). This operation is conventional and widely used in the current ethanol production industry.

The residual solids from the fermentation stage may contain non-fermentable materials that may also contain significant levels of useful proteins or amino acids. This solids fraction could be combined with other animal feed products or, depending on the exact nature of the material (based on the feedstock), further processed, via drying, to produce a specialized teed product.

Example 3

Corncob (Corn Feedstock)

Corn cobs are a major co-product from the production of corn starches for fermentation into ethanol. Corn cobs are the material remaining after the corn kernels are removed. Much of this material is plowed back into the field as a nutrient component, soil amendment, or burned for energy recovery.

The quantities of this material are significant. For example, a typical acre of corn will yield 160 bushels of corn and 1200 pounds of corn cobs. In 2010 the U.S. corn acreage was estimated at 90 million tons which will generate over 49 million tons of cobs. In general, the cobs from corn contains about 45% cellulose, and 40% hemicelluloses carbohydrate (which if properly prepared could serve as a fermentation feed) generating 38 million tons of cellulose derived glucose, non food feed stocks for fermentation into ethanol.

It should be noted that with preparation, the resulting sugars consist of both C6 (hexose) and C5 (pentose) fractions. The C6 fraction is fermentable via the use of standard yeast materials. C5 sugars will not ferment with yeasts only, and specialized organisms have been developed that will convert C5's. In addition, there are other processes that have been developed that utilize C5 sugars to produce other (non-ethanol) products.

Significant advantages could be brought about in the biofuels industries if this feedstock could be processed to generate ethanol. Incorporation of corn cob treatment operations within existing ethanol plants could further enhance the potential economic attractiveness.

To assess the potential for the process to handle this feed, samples of corn cob granule material were collected from Grit-o-Cob, a corn cob material sold as a sand blasting media. The basic testing approach was as follows:

- The corn cob granules were further ground to a particle size of 400 mesh to allow for ease of feeding as a slurry to the continuous reactor system 100 g of cob material was mixed with 100 g methanol and 100 g water then reacted at 280 C and 2100 psi for 30 minutes.
- After reaction, the glucose and methyl glucoside product mass was then filtered and washed with water to separate unreacted solids from the glucose and methyl glucoside (and other) bearing liquid.
- The solids fraction was then set aside.
- The liquid fraction was then heated to remove excess alcohol (that would be recovered for recycle in a commercial scenario).
- With the reaction conditions employed, derivatized sugars, such as 5-hydroxymethylfurfural, could be formed which will allow for potential production and recovery of other products.

The reaction mixture was analyzed on an HPLC device and results showed the presence of glucose and methyl glucoside.

Example 4

Rice Husk

Rice husk is a major residue from the production of rice for food. Rice husk is the material remaining after the rice kernel and rice bran are removed. Much of this material is waste that is piled, dumped or bunted for energy recovery.

The quantities of this material are significant. For example, in 2010 the world rice acreage was estimated at greater than 475 million tons which will generate over 104.5 million tons of husk. In general, the husk from corn contains about 35% cellulose, and 25% hemicelluloses carbohydrates (which if properly prepared could serve as a fermentation feed) generating roughly 60 million tons of cellulose derived glucose, non food feed stocks for fermentation into ethanol.

It should be noted that with preparation, the resulting sugars consist of both C6 and C5 fractions. The C6 fraction is fermentable via the use of standard yeast materials. C5 sugars will not ferment with yeasts only, and specialized organisms have been developed that will convert C5's. In addition, there are other processes that have been developed that utilize C5 sugars to produce other (non-ethanol) products.

Significant advantages could be brought about in the biofuels industries if this feedstock could be processed to generate ethanol. Incorporation of rice husk treatment operations within existing ethanol plants could further enhance the potential economic attractiveness.

To assess the potential for the process to handle this feed, samples of rice husk material were collected from Wilmar Company, one of the world's largest rice producers and palm products. The basic testing approach was as follows:

The rice husks were further ground to a panicle size of 400 mesh to allow for ease of feeding as a slurry to the continuous reactor system. 100 g of rice husk material was mixed with 100 g methanol and 100 g water then reacted at 280 C and 2100 psi for 30 minutes.

After reaction, the glucose and methyl glucoside product mass was then filtered and washed with water to separate unreacted solids from the glucose and methyl glycoside (and other) bearing liquid.

The solids fraction was then set aside.

The liquid fraction was then heated to remove excess alcohol (that would be recovered for recycle in a commercial scenario).

With the reaction conditions employed, derivatized sugars, such as 5-hydroxymethylfurfural, could be formed which will allow for potential production and recovery of other products.

The reaction mixture was analyzed on an HPLC device and results showed the presence of glucose and methyl glycoside.

We claim:

1. A method for making an alkyl glucoside or an alkyl pentoside, and optionally making a sorbitol or a polyhydric alcohol, the method comprising:
   (a) (i) combining a feedstock with an alcohol and water, wherein the feedstock comprises a cellulosic material, a protein, or both; or
   (ii) combining a feedstock with an alcohol and water, wherein the feedstock comprises a cellulosic material, a hemicellulose material, or both;
   (b) reacting the feedstock and the alcohol and water at a temperature in the range of between about 140° C. and 350° C., and at a pressure in a range of between about 400 psig and 3500 psig to cleave the cellulosic material to generate a reaction product comprising an alkyl glucoside or an alkyl pentoside, wherein:
   (i) the feedstock contains at least about 10 wt % cellulosic material based on the dry weight of the feedstock;
   (ii) the feedstock contains at least about 10 wt % proteins based on the dry weight of the feedstock;
   (iii) the water content of the combination of (a) before reaction is between about 30 wt % and 300 wt % of the dry weight of the feedstock; or
   (iv) the alcohol is in an amount from between about 0.5% and 350% wt excess of the hexose or pentose in the feedstock;
   and
   (c) separating or isolating the alkyl glucoside or alkyl pentoside from the reaction product of the reaction of (b).

2. The method of claim 1, wherein the feedstock contains at least about 10 wt % cellulosic material based on the dry weight of the feedstock.

3. The method of claim 1, wherein the feedstock contains at least about 10 wt % proteins based on the dry weight of the feedstock.

4. The method of claim 1, wherein the water content of the combination of (a) before reaction is between about 30 wt % and 300 wt % of the dry weight of the feedstock.

5. The method according to claim 1, wherein said feedstock comprises:

(a) rice husk, rice bran, corn stover, corn cobs, sugar cane bagasse, palm fiber, palm kernel cake, wood pulp, pine tree material, fir tree material, hardwood tree material, switch grass, microalgae, macro algae or cyanobacteria, or any combination thereof; or
(b) a cyanobacteria, a lignocellulose, a cellulose, a polysaccharide, or any combination thereof.

6. The method of claim 1, wherein the alcohol comprises a methanol, ethanol or propanol, or any combination thereof.

7. The method of claim 1, wherein the alcohol is in an amount from between about 0.5% and 350% wt excess of the hexose or pentose in the feedstock.

8. The method of claim 1, wherein the hydrogenation catalyst comprises a heterogeneous catalyst or a homogenous catalyst,
   wherein optionally the hydrogenation catalyst comprises a catalyst metal,
   and optionally the catalyst metal is selected from the group consisting of a platinum, a palladium, a rhodium, a ruthenium, a rainey nickel or a copper chromite.

9. The method of claim 1, wherein the temperature is in the range of between about 180° C. and 350° C.

10. The method of claim 1, wherein the temperature is in the range of between about 240° C. and 350° C.

11. The method of claim 1, wherein the pressure is in the range of between about 400 psig and 3500 psig.

12. The method of claim 1, wherein the pressure is in the range of between about 1500 psig and 3500 psig.

13. A method for making a hexose, an alkyl glucoside, a pentose, or an alkyl pentoside, and optionally making a sorbitol or a polyhydric alcohol, the method comprising:
   (a) combining a feedstock with an alcohol and water, wherein the feedstock comprises:
   (i) (1) a polysaccharide, (2) at least 10 wt % cellulosic material based on the dry weight of the feedstock, and (3) at least 10 wt % proteins based on the dry weight of the feedstock; or
   (ii) (1) a polysaccharide, and (2) at least 10 wt % cellulosic material based on the dry weight of the feedstock;
   (b) (i) reacting the feedstock and the alcohol and water at a temperature in the range of between about 240° C. to 350° C., and at a pressure in a range of between about 1500 psig to 3500 psig to generate reaction product comprising a hexose and an alkyl glucoside, and/or a pentose and an alkyl pentoside, and if proteins are present the reaction product further comprises amino acids; or
   (ii) reacting the feedstock and the alcohol and water at a temperature in the range of between about 240° C. and 350° C., and at a pressure in a range of 1500 psig and 3500 psig, to generate a reaction product comprising a hexose and an alkyl glucoside, and/or a pentose and an alkyl pentoside;
   and
   (c) separating or isolating the alkyl glucoside or alkyl pentoside from the reaction product of the reaction of (b).

14. The method of claim 13, wherein the water content of the combination of (a) before reaction is between about 30 wt % and 300 wt % of the dry weight of the feedstock.

15. The method of claim 13, wherein the feedstock comprises:
   (a) a cyanobacteria, a lignocellulose, a cellulose, a polysaccharide, or any combination thereof, or
   (b) a rice husk, a rice bran, a corn stover, a corn cob, a sugar cane bagasse, a palm fiber, a palm kernel cake, a wood pulp, a pine tree material, a fir tree material, a hardwood tree material, a switch grass, a microalgae, a macro algae, a cyanobacteria, or any combination thereof.

16. The method of claim 1, further comprising hydrolyzing the alkyl glucoside using a weak acid and additional water, wherein the resulting mixture is a glucose and an alcohol.

17. The method of claim 16, further comprising removing the alcohol, optionally removing the alcohol by evaporation, centrifuge separation or crystallization.

18. The method of claim 13, further comprising hydrolyzing the alkyl glucoside using a weak acid and additional water, wherein the resulting mixture is a glucose and an alcohol.

19. The method of claim 18, further comprising removing the alcohol, optionally removing the alcohol by evaporation, centrifuge separation or crystallization.

20. The method of claim 13, wherein the hydrogenation catalyst comprises a heterogeneous catalyst or a homogenous catalyst.

21. The method of claim 20, wherein the hydrogenation catalyst comprises a catalyst metal, and optionally the catalyst metal is selected from the group consisting of a platinum, a palladium, a rhodium, a ruthenium, a rainey nickel or a copper chromite.

22. The method of claim 1, wherein the reaction product is in the form of a reaction product slurry having an insoluble solids portion and a liquid fraction, and the reaction product slurry optionally comprises any unreacted feedstock, glucose, alkyl glucosides, sorbitol, excess alcohol, water, lignin, organic salts, inorganic salts.

23. The method of claim 1, further comprising separating or isolating the alkyl glucoside or alkyl pentoside by a method comprising:

transferring the reaction product slurry to a Liquid/Solid Separation system to separate the liquid water phase fraction from the insoluble solids portion, including any lignin if contained in the feed, wherein glucose and alkyl glucosides remain with the liquid water phase fraction, and optionally the separated alkyl glucoside is hydrolyzed using weak acid and additional water, and the resulting mixture comprises glucose and alcohol, and optionally the alcohol is removed by evaporation, centrifuge separation, crystallization or a combination thereof, and optionally separating the liquid water phase fraction from the insoluble solids portion comprises use of filtration, carbon treatment, centrifugation or a combination thereof, and optionally the insoluble solids portion is washed with alcohol, water or hydrophobic solvent and sent to storage for re-processing or discharge.

24. The method of claim 1, further comprising a method for making a sorbitol or a polyhydric alcohol by further reacting the reaction product of step (b) by addition of:
  (i) a hydrogen and a hydrogenation catalyst, or
  (ii) a hydrogenation catalyst;
  wherein the presence of the hydrogen and the hydrogenation catalyst, or the hydrogenation catalyst, in the reaction mixture generates a sorbitol or a polyhydric alcohol and a sugar derivative,
  and optionally the amount of hydrogen ranges from between 1:1 mole wt of the glucose in the feedstock to 1000:1 mole wt of the contained glucose in the feedstock.

25. The method of claim 13, wherein the reaction product is in the form of a reaction product slurry having an insoluble solids portion and a liquid fraction, and the reaction product slurry optionally comprises any unreacted feedstock, glucose, alkyl glucosides, sorbitol, excess alcohol, water, lignin, organic salts, inorganic salts.

26. The method of claim 13, wherein separating or isolating the alkyl glucoside or alkyl pentoside comprises:

transferring the reaction product slurry to a Liquid/Solid Separation system to separate the liquid water phase fraction from the insoluble solids portion, including any lignin if contained in the feed, wherein glucose and alkyl glucosides remain with the liquid water phase fraction, and optionally the separated alkyl glucoside is hydrolyzed using weak acid and additional water, and the resulting mixture comprises glucose and alcohol, and optionally the alcohol is removed by evaporation, centrifuge separation, crystallization or a combination thereof, and optionally separating the liquid water phase fraction from the insoluble solids portion comprises use of filtration, carbon treatment, centrifugation or a combination thereof, and optionally the insoluble solids portion is washed with alcohol, water or hydrophobic solvent and sent to storage for re-processing or discharge.

27. The method of claim 13, further comprising a method for making a sorbitol or a polyhydric alcohol by further reacting the reaction product of step (b) by addition of:
  (i) a hydrogen and a hydrogenation catalyst, or
  (ii) a hydrogenation catalyst;
  wherein the presence of the hydrogen and the hydrogenation catalyst, or the hydrogenation catalyst, in the reaction mixture generates a sorbitol or a polyhydric alcohol and a sugar derivative,
  and optionally the amount of hydrogen ranges from between 1:1 mole wt of the glucose in the feedstock to 1000:1 mole wt of the contained glucose in the feedstock.

* * * * *

UNITED STATES PATENT AND TRADEMARK OFFICE
CERTIFICATE OF CORRECTION

PATENT NO. : 9,605,325 B2  
APPLICATION NO. : 15/163160  
DATED : March 28, 2017  
INVENTOR(S) : William W. Berry et al.

Page 1 of 1

It is certified that error appears in the above-identified patent and that said Letters Patent is hereby corrected as shown below:

On the Title Page

Under Item (63), Related U.S. Application Data, please change text to the following:
Continuation of application No. 13/882,986, filed July 31, 2013, now Pat. No. 9,346,843, issued May 24, 2016, which claims benefit of priority to PCT application PCT/US2014/053594, filed November 1, 2011, which claims benefit of priority to U.S. provisional application serial no. 61/409,395, filed November 02, 2010.

Signed and Sealed this
Twenty-sixth Day of June, 2018

Andrei Iancu
*Director of the United States Patent and Trademark Office*